US007008434B2

(12) United States Patent
Kurz et al.

(10) Patent No.: US 7,008,434 B2
(45) Date of Patent: *Mar. 7, 2006

(54) CLOT RETRIEVAL DEVICE (75) Inventors: Daniel R. Kurz, Sunnyvale, CA (US); David A. Ferrera, San Francisco, CA (US)

(73) Assignee: Micrus Corporation, Mountain View, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/754,660

(22) Filed: Jan. 8, 2004

(65) Prior Publication Data

US 2004/0153110 A1    Aug. 5, 2004

Related U.S. Application Data (60) Continuation of application No. 10/023,028, filed on Dec. 17, 2001, now Pat. No. 6,692,504, which is a division of application No. 09/312,931, filed on May 17, 1999, now Pat. No. 6,350,271.

(51) Int. Cl.
    *A61B 17/22*    (2006.01)

(52) U.S. Cl. .................... 606/127; 606/159; 606/110; 604/106

(58) Field of Classification Search .............. 606/1, 606/110–114, 127, 128, 159, 190–200, 78, 606/108, 151, 157, 167, 213; 604/109–113, 604/96.01–109; 600/201, 204, 206–210
See application file for complete search history.

(56) References Cited

U.S. PATENT DOCUMENTS

| | | | |
|---|---|---|---|
| 2,556,783 A * | 6/1951 | Wallace | 606/127 |
| 3,868,956 A * | 3/1975 | Alfidi et al. | 606/198 |
| 4,299,225 A | 11/1981 | Glassman | |
| 4,425,908 A | 1/1984 | Simon | |
| 4,612,931 A | 9/1986 | Dormia | |
| 4,765,332 A | 8/1988 | Fischell et al. | |
| 4,873,978 A | 10/1989 | Ginsburg | |
| 4,919,133 A | 4/1990 | Chiang | |
| 5,009,659 A * | 4/1991 | Hamlin et al. | 606/159 |
| 5,071,407 A | 12/1991 | Termin et al. | |
| 5,108,406 A | 4/1992 | Lee | |
| 5,108,407 A * | 4/1992 | Germeia et al. | 606/108 |
| 5,129,910 A * | 7/1992 | Phan et al. | 606/127 |
| 5,192,286 A | 3/1993 | Phan et al. | |
| 5,201,741 A | 4/1993 | Dulebohn | |
| 5,324,304 A | 6/1994 | Rasmussen | |
| 5,330,482 A | 7/1994 | Gibbs et al. | |
| 5,342,371 A | 8/1994 | Welter et al. | |
| 5,421,832 A | 6/1995 | Lefebvre | |

(Continued)

FOREIGN PATENT DOCUMENTS

WO    WO 96/01591    1/1996

*Primary Examiner*—Glenn K. Dawson
(74) *Attorney, Agent, or Firm*—Fulwider Patton Lee & Utecht, LLP (57) ABSTRACT

The shape memory clot retrieval device can be placed in the vasculature of a patient for retrieving and removing distal clots. The clot retrieval device has an elongated catheter member that can be inserted in the vasculature, with one or more clot retrieval members on the elongated catheter member that are movable between an initial compressed configuration in which the clot retrieval device is inserted into the vasculature and an expanded configuration extending outwardly from the elongated catheter member to trap and hold clots within the vessel. The clot retrieval device typically can be introduced to the desired treatment site in the vasculature through a guiding catheter.

5 Claims, 4 Drawing Sheets

U.S. PATENT DOCUMENTS

| | | |
|---|---|---|
| 5,496,330 A | 3/1996 | Bates et al. |
| 5,601,595 A | 2/1997 | Smith |
| 5,665,098 A | 9/1997 | Kelly et al. |
| 5,669,933 A | 9/1997 | Simon et al. |
| 5,697,936 A | 12/1997 | Shipko et al. |
| 5,702,413 A * | 12/1997 | Lafontaine .................. 606/159 |
| 5,725,543 A | 3/1998 | Redha |
| 5,792,145 A | 8/1998 | Bates et al. |
| 5,800,525 A | 9/1998 | Bachinski et al. |
| 5,814,064 A | 9/1998 | Daniel et al. |
| 5,827,304 A * | 10/1998 | Hart .......................... 606/159 |
| 5,827,324 A | 10/1998 | Cassell et al. |
| 5,846,260 A | 12/1998 | Maahs |
| 5,984,965 A * | 11/1999 | Knapp et al. ................. 623/12 |
| 6,066,149 A * | 5/2000 | Samson et al. ............. 606/127 |
| 6,350,271 B1 * | 2/2002 | Kurz et al. ................. 606/159 |
| 6,692,504 B1 * | 2/2004 | Kurz et al. ................. 606/127 |

* cited by examiner

CLOT RETRIEVAL DEVICE

RELATED APPLICATIONS

This is a continuation of Ser. No. 10/023,028 filed Dec. 17, 2001, now U.S. Pat. No. 6,692,504, which is a divisional of Ser. No. 09/312,931 filed May 17, 1999, now U.S. Pat. No. 6,350,271.

BACKGROUND OF THE INVENTION

1. Field of the Invention

This invention relates generally to medical instruments for retrieving and withdrawing clots from the vasculature, and more particularly concerns a shape memory clot retrieval device having an elongated catheter member with at least one clot retrieval member connected to the elongated catheter member that is movable between an initial compressed configuration in which the clot retrieval device is inserted into the vasculature and an expanded configuration extending outwardly from the elongated catheter member to trap and hold clots within the vessel.

2. Description of Related Art

Recently developed interventional procedures have been used to treat defects in the vasculature which are not easily reached by surgical procedures. More particularly, such interventional procedures have been developed to treat defects that are located in small and remote vessels such as those within the brain. During such interventional procedures, vasoocclusive devices are typically placed within the vasculature of the human body by use of a catheter, either to block the flow of blood through a vessel making up that portion of the vasculature through the formation of an embolus, or to form such an embolus within an aneurysm stemming from the vessel. When an embolus generating vasoocclusive device is used to treat an aneurysm, the success of the treatment generally depends upon whether the embolus generating vasoocclusive device can migrate out of the aneurysm through the neck of the aneurysm. Migration of the embolus generated out of the aneurysm into the parent vessel poses a danger to the patient, so that it would be desirable to provide a device for retrieving and withdrawing such an embolus, whether the embolus has been created by an embolus generating vasoocclusive device or otherwise.

One conventional technique for retrieving deleterious materials such as an embolus from body lumens involves the use of a retrieval catheter having a slack net at its distal end that is operated by a pull wire, that may be collapsed to facilitate introduction of the catheter into a body lumen, and that may be opened when necessary to permit capture and retrieval of the deleterious materials. The slack net structure is secured to a flexible loop member which is secured to the pull wire, and the flexible loop member is formed from resilient materials possessing a memory so that when pull wire is retracted, the loop member will regain a preset circular configuration. However, such a structure is relatively bulky and cumbersome, making the technique difficult to employ in more distal areas of the vasculature with narrow lumens, such as in the brain.

A catheter apparatus is also known that employs a shape memory alloy structure as an actuator for a thin shutter door to open and close a radially disposed opening in the catheter for collecting plaque. While this apparatus is suitable for collecting plaque on the inside of a blood vessel, it is not generally effective for retrieving and withdrawing an embolus that may be loose or free floating within the vasculature. Another known technique uses an adjustable closed wire loop or snare that is manipulated over an object to be retrieved, and in one such apparatus, the surgical snare is made from a shape memory material that can be trained to remember a specific configuration. However, these types of surgical snares can require great care and dexterity for their operation in acquiring an embolus, and an embolus can easily escape, so that it would be desirable to provide a system for retrieving and withdrawing an embolus within the vasculature of a patient that can be deployed in narrow, distal vessels for trapping and holding distal loose or free floating clots. The present invention meets these needs.

SUMMARY OF THE INVENTION

Briefly, and in general terms, the present invention provides for an improved shape memory clot retrieval device that can be placed in the vasculature of a patient for retrieving and removing distal clots. The clot retrieval device advantageously has an elongated catheter member that can be inserted in the vasculature, with one or more clot retrieval members on the elongated catheter member that are movable between an initial compressed configuration in which the clot retrieval device is inserted into the vasculature and an expanded configuration extending outwardly from the elongated catheter member to trap and hold clots within the vessel. The clot retrieval device typically can be introduced to the desired treatment site in the vasculature through a delivery catheter.

The invention accordingly provides for an apparatus for removing clots from the vasculature of a patient, comprising an elongated catheter member, and one or more clot retrieval members connected to the elongated catheter member. The one or more clot retrieval members are advantageously formed from a shape memory material so that they are movable upon activation between an initial compressed configuration and an expanded configuration extending outwardly from the elongated catheter member to trap and hold clots within the vessel. The elongated catheter member is adapted to be placed within a vessel of the patient when the one or more clot retrieval members are in the compressed configuration, and is adapted to be removed from the vessel when the clot retrieval members are in the expanded configuration, whereby clots trapped by the clot retrieval members can be withdrawn from the vessel. In a presently preferred aspect, the clot retrieval members are formed from a shape memory material, preferably having a glass transition temperature ($T_g$) above body temperature, and having a desired compressed configuration at a temperature appropriate for introduction into the body via a catheter, and an expanded configuration with the one or more clot retrieval members extending outwardly that is assumed upon activation.

The shape memory material is currently preferably a shape memory polymer, such as polyurethane, heat shrink tubing such as polyethylene, polyethylene terephthalate (PET) or high density polyethylene (HDPE), although the shape memory material may alternatively be a shape memory metal such as nickel titanium alloy, such as that available under the trade name NITINOL, for example, that can be heat treated to have shape memory behavior. As the clot retrieval members are activated by heat, the activated shape memory clot retrieval members open radially and outwardly to catch and hold clots in the vasculature.

A heat activation member is also preferably provided for heating the one or more clot retrieval members to cause them to expand radially outwardly from the elongated catheter member. In a presently preferred aspect, the heat activation member typically can be advanced axially through the middle of the elongated catheter member and the one or more clot retrieval members to be positioned adjacent to the one or more clot retrieval members. The heat activation member currently preferably comprises an optical fiber, although the heat activation member can also comprise a heat pipe, or a device for generating heat by RF energy, or the like.

In one presently preferred embodiment, the elongated catheter member is tubular, and the one or more clot retrieval members comprise a tubular member formed from a shape memory material having a tubular wall defining a plurality of ridges and valleys. The ridges and valleys are movable between an initial compressed configuration in which the ridges and valleys are substantially flattened, to an expanded configuration wherein the ridges extend outwardly from the valleys of the elongated catheter member to trap and hold clots within the vessel. The elongated catheter member is thus adapted to be placed within a vessel of the patient when the plurality of ridges and valleys are in the compressed, flattened configuration and removed from the vessel when the ridges and valleys are in the expanded configuration, whereby clots trapped by the ridges and valleys can be withdrawn from the vessel. In a presently preferred aspect, the ridges and valleys of the clot retrieval tubular member are initially compressed axially, radially, or both.

In another presently preferred embodiment, the one or more clot retrieval members comprise a plurality of tab members connected to the elongated catheter member. The plurality of tab members are movable between an initial compressed configuration to an expanded configuration extending outwardly from the elongated catheter member to trap and hold clots within the vessel, and the elongated catheter member is adapted to be placed within a vessel of the patient when the tab members are in the compressed configuration and removed from the vessel when the tab members are in the expanded configuration, whereby clots trapped by the tab members can be withdrawn from the vessel.

In one presently preferred embodiment, the elongated catheter member comprises an elongated, tubular member, and the one or more clot retrieval members are formed from the tubular wall of the elongated tubular member, defining a plurality of tab members that are initially compressed axially, radially, or both to extend contiguously with the surface of the tubular wall. In a preferred aspect, the elongated tubular member and tab members are formed from a shape memory material.

In an alternate preferred embodiment, the elongated catheter member carries one or more clot retrieval members that can comprise an annular ring, preferably formed from a shape memory material, connected to the elongated catheter member, with the annular ring having an initial compressed configuration in which the annular ring is compressed radially against the surface of the elongated catheter member, and an expanded configuration in which the annular ring projects outwardly from the surface of the elongated catheter member, whereby the extended annular ring can trap and hold a blood clot.

In another presently preferred alternate embodiment, the elongated catheter member carries a plurality of tab members, with each of the tab members being connected at one end to the elongated catheter member and having a free end, with the tab members having an initial compressed configuration in which the tab members are compressed against the surface of the elongated catheter member and an expanded configuration in which the tab members project outward radially from the surface of the elongated catheter member, whereby the extended tab members can trap and hold a blood clot. The tab members can be initially compressed axially, radially, or both. In a presently preferred aspect, the tab members are formed from a shape memory material.

In yet another presently preferred embodiment, the apparatus for removing clots comprises an elongated catheter member and the clot retrieval member comprises an elongated sheet or ribbon of shape memory material having first and second ends connected to the elongated catheter member, with the elongated sheet of shape memory material wound in a helical configuration about the elongated catheter member. The ribbon of shape memory material has an initial compressed configuration in which the ribbon of shape memory material is compressed radially against the surface of the elongated catheter member and an expanded configuration in which the ribbon of shape memory material projects outward radially from the surface of the elongated catheter member, whereby the extended ribbon of shape memory material can trap and hold a blood clot.

These and other aspects and advantages of the invention will become apparent from the following detailed description and the accompanying drawings, which illustrate by way of example the features of the invention.

DETAILED DESCRIPTION OF THE PREFERRED EMBODIMENTS

While one method of treatment of an aneurysm or arteriovenous malformation can involve creation of an embolus by an embolus generating vasoocclusive device, the potential migration of such an embolus into the vasculature of a patient can pose a risk to the patient. Techniques have been developed for scavenging such an embolus from the vasculature, but they have generally proved to be difficult to employ in the more distal, narrow areas of the vasculature, such as in the brain.

Figure 1:
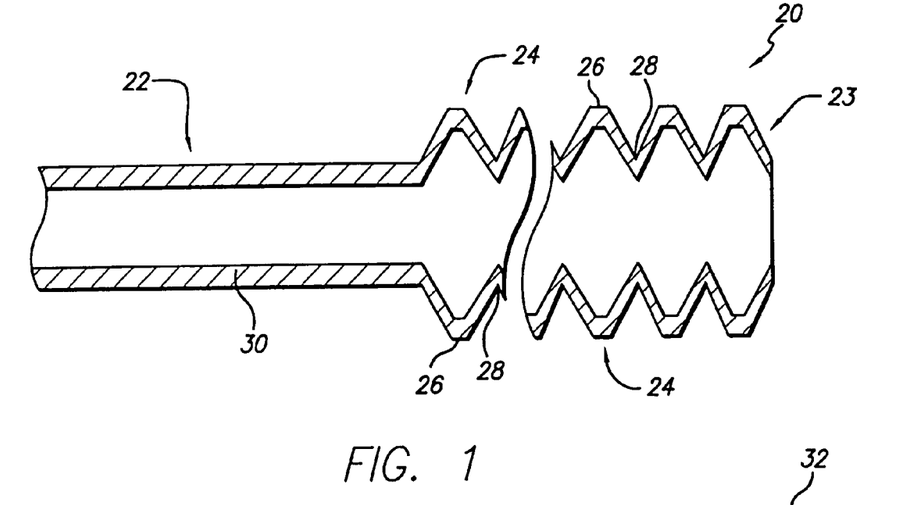
FIG. 1 is a cross-sectional view of a first preferred embodiment of a clot retrieval device according to the present invention, showing the clot retrieval member in a precompressed state.
Figure 2:
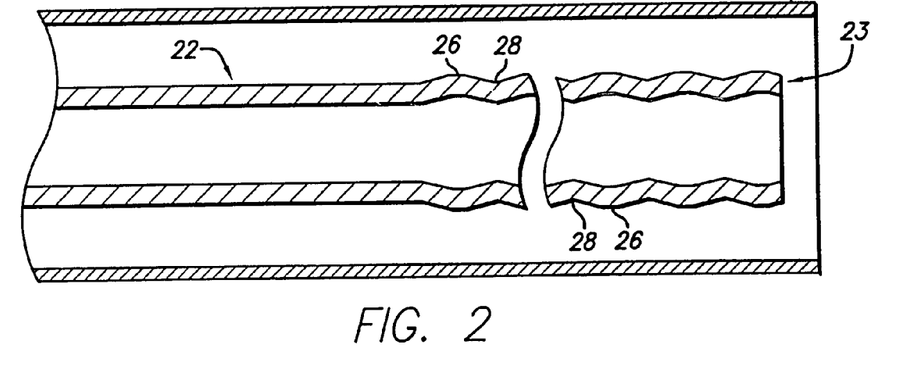
FIG. 2 is a cross-sectional view of the clot retrieval device of FIG. 1, following compression of the clot retrieval member.
Figure 3:
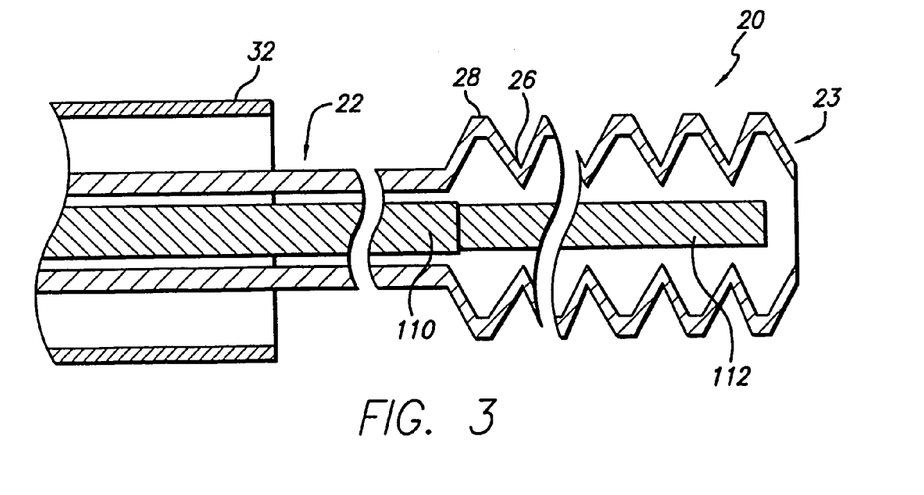
FIG. 3 is a cross-sectional view of the clot retrieval device of FIG. 1, following expansion of the clot retrieval member by heat activation.

As is illustrated in the drawings, the invention is embodied in a clot retrieval apparatus 20 for removing clots from the vasculature of a patient. With reference to FIGS. 1 to 3, in one presently preferred embodiment, the clot retrieval apparatus includes an elongated catheter member 22, and a clot retrieval portion 23 having one or more clot retrieval members 24 connected to the elongated catheter member. The clot retrieval members are movable between an initial compressed configuration illustrated in FIG. 2, to an expanded configuration, illustrated in FIG. 3, extending outwardly from the elongated catheter member to trap and hold clots within the vessel. The clot retrieval apparatus is thus adapted to be placed within a vessel of the patient when the clot retrieval members are in the compressed configuration, and is adapted to be deployed within the vessel of the patient to move the one or more clot retrieval members to their expanded configuration. Thereafter, the clot retrieval apparatus can be removed from the patient's vessel, to retrieve and remove any clots that may be trapped by the clot retrieval members.

In a presently preferred aspect of the first embodiment of the clot retrieval apparatus, the elongated catheter member is tubular, and the clot retrieval members are formed as a plurality of ridges 26 and valleys 28 in the tubular wall 30 of the elongated catheter member. The plurality of ridges and valleys can be formed in an expanded, precompressed configuration as shown in FIG. 1, and then compressed axially, radially, or both, under heat and pressure, to the compressed configuration shown in FIG. 2, in which the ridges and valleys are substantially contiguous and substantially flattened, typically having a maximum compressed outer diameter of about 0.014 inch, to an expanded configuration shown in FIG. 3 in which the ridges extend outwardly from the elongated catheter member to trap and hold clots within the vessel. The elongated catheter member is adapted to be delivered through a placement or guiding catheter 32, placed within a vessel of the patient with the plurality of ridges and valleys in the compressed configuration, expanded by heat activation, and removed through the guiding catheter from the vessel when the ridges and valleys are in the expanded configuration, so that clots trapped by the ridges and valleys can be withdrawn from the vessel. Typically the ridges are formed in the pre-compression stage to have an expanded outer diameter ranging from about 0.014 to about 0.025 inches, so that the guiding catheter will have an inner diameter greater than this so that the clot retrieval portion can be withdrawn through the guiding catheter in the expanded configuration to withdraw clots retrieved from the vasculature. The clot retrieval portion is preferably formed from a shape memory material having a glass transition temperature ($T_g$) above body temperature, with a desired compressed configuration at a temperature appropriate for introduction into the body via a catheter, and having an expanded configuration for trapping and holding clots.

Figure 4:
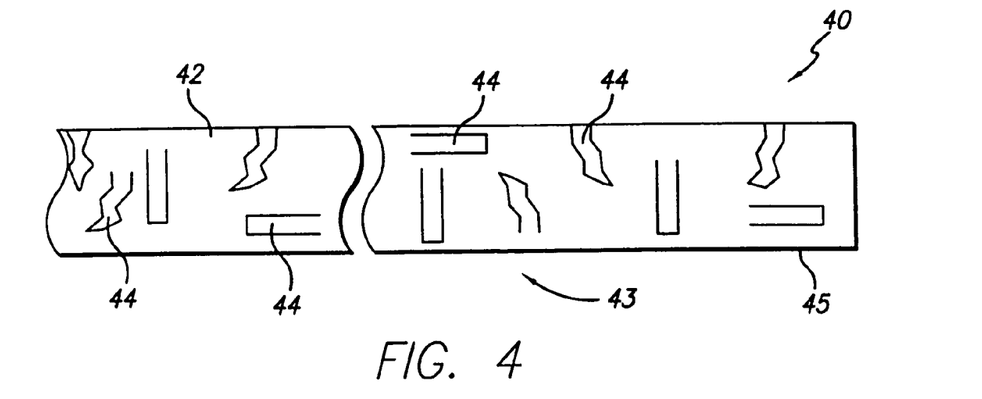
FIG. 4 is a side elevational view of a second preferred embodiment of a clot retrieval device according to the present invention, showing the clot retrieval members in a precompressed state.
Figure 5:
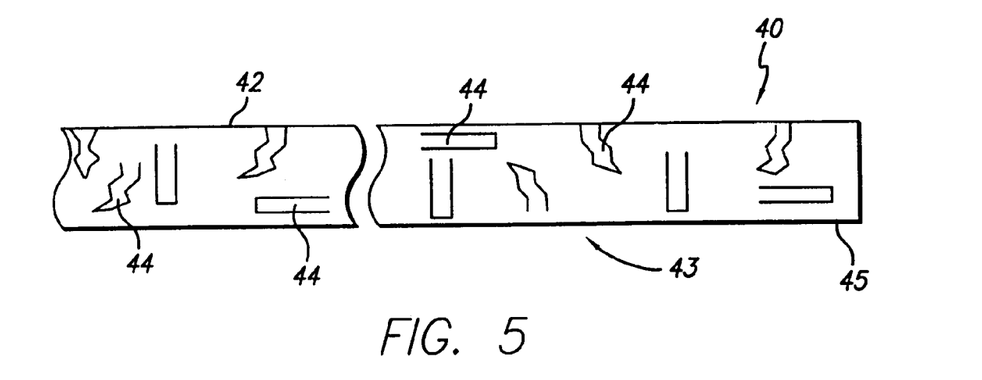
FIG. 5 is a side elevational view of the clot retrieval device of FIG. 4, following compression of the clot retrieval members.
Figure 6:
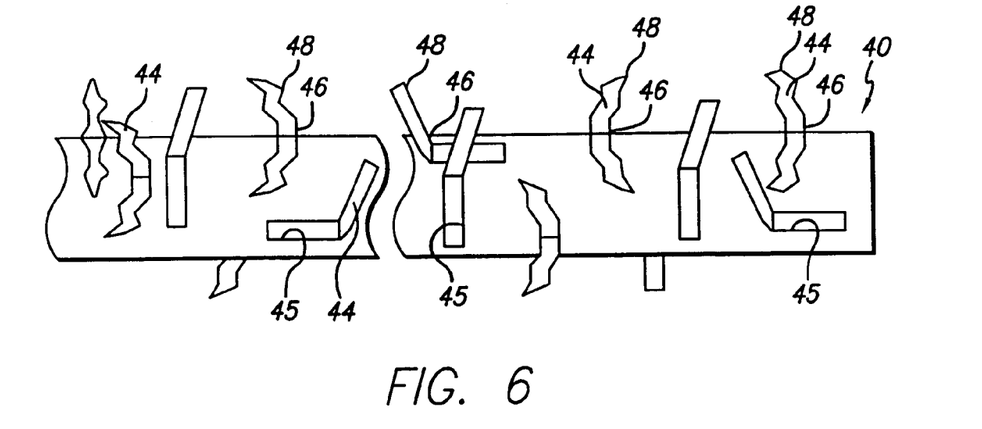
FIG. 6 is a side elevational view of the clot retrieval device of FIG. 4, following expansion of the clot retrieval members by heat activation.

Referring to FIGS. 4, 5 and 6, in an alternate preferred embodiment provides for a clot retrieval apparatus 40 for removing clots from the vasculature of a patient, having an elongated, tubular catheter member 42, and a clot retrieval portion 43. The clot retrieval portion includes a plurality of tab members or fingers 44 cut from the tubular wall 45 of the elongated catheter member to have a first end 46 connected to the elongated catheter member, and a free end 48. The clot retrieval members are movable between an initial compressed configuration illustrated in FIG. 5, and an expanded configuration illustrated in FIG. 6 extending outwardly from the elongated catheter member to trap and hold clots within the vessel. The elongated catheter member is adapted to be delivered through a guiding catheter as described above, for placement within a vessel of the patient when the tab members are in the compressed configuration, and the clot retrieval portion and tab members are dimensions so as to be removable from the vessel through the guiding catheter when the tab members are in the expanded configuration, such that clots trapped by the tab members can be withdrawn from the vessel. The tubular wall of the elongated tubular catheter member and the tab members are preferably formed from a shape memory material, and the tab members are initially compressed axially, radially, or both to be substantially flattened to extend substantially contiguously with the exterior surface of the tubular wall of the tubular catheter member.

Figure 7:
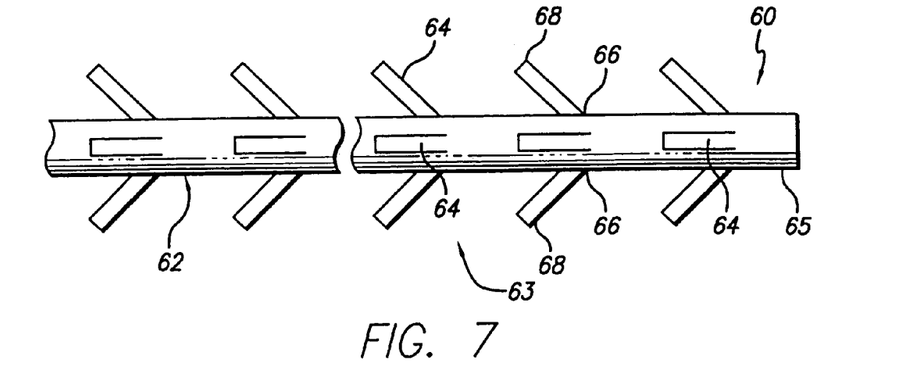
FIG. 7 is a side elevational view of a third preferred embodiment of a clot retrieval device according to the present invention, showing the clot retrieval members in an expanded state.
Figure 8:
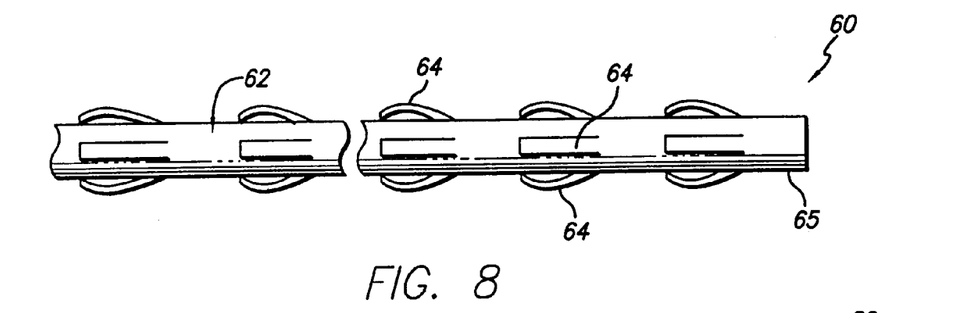
FIG. 8 is a side elevational view of the clot retrieval device of FIG. 7, showing the clot retrieval members in a compressed state.

With reference to FIGS. 7 and 8, in another alternate preferred embodiment, a clot retrieval apparatus 60 is provided for removing clots from the vasculature of a patient, having an elongated, tubular catheter member 62, and a clot retrieval portion 63 having a plurality of tab members or fingers 64 projecting from the tubular wall 65 of the elongated catheter member. The tab members or fingers have a first end 66 connected to the elongated catheter member, and a free end 68. In this embodiment, the tab members 64 are currently preferably attached to the elongated, tubular catheter member such as by an adhesive, such as cyanoacrylate adhesive, for example, and are movable between an initial compressed configuration shown in FIG. 8, to an expanded configuration illustrated in FIG. 7 extending radially outwardly from the elongated catheter member to trap and hold clots within the vessel. The elongated catheter member is adapted to be delivered through a guiding catheter as described above, to be placed within a vessel of the patient when the tab members are in the compressed configuration. The elongated catheter member and clot retrieval portion are dimensioned so as to be removable from the vessel through the guiding catheter when the tab members are in the expanded configuration, such that clots trapped by the tab members can be withdrawn from the vessel. The tubular wall of the elongated tubular catheter member and the tab members are preferably formed from a shape memory material, and the tab members are initially compressed axially, radially, or both to be substantially flattened to extend contiguously with the exterior surface of the tubular wall of the tubular catheter member.

Figure 9:
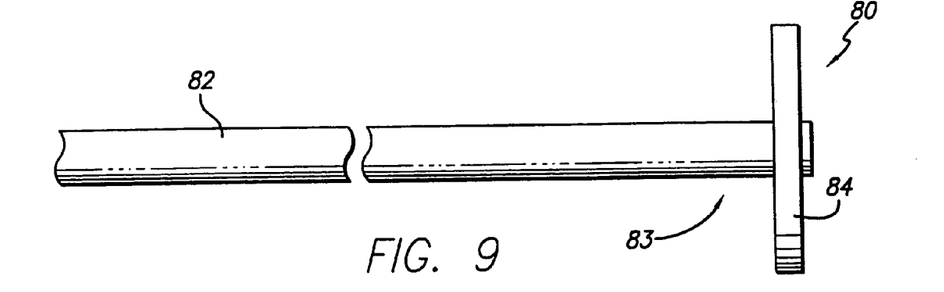
FIG. 9 is a side elevational view of a fourth preferred embodiment of a clot retrieval device according to the present invention, showing the clot retrieval member in an expanded state.
Figure 10:
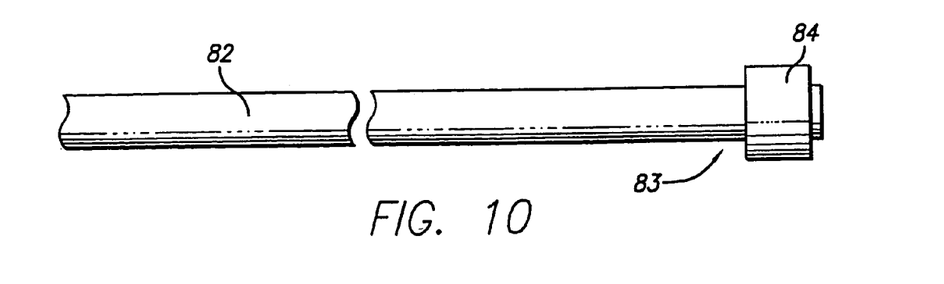
FIG. 10 is a side elevational view of the clot retrieval device of FIG. 9, showing the clot retrieval member in a compressed state.

In another presently preferred alternate embodiment illustrated in FIGS. 9 and 10, the invention provides for a clot retrieval apparatus 80 for removing clots from the vasculature of a patient, having an elongated, tubular catheter member 82, and a clot retrieval portion 83 having an annular ring 84 connected to the elongated catheter member. The annular ring can be activated to transform from an initial compressed configuration illustrated in FIG. 10 in which the annular ring is compressed radially against the surface of the elongated catheter member, to an expanded configuration illustrated in FIG. 9, in which the annular ring projects outwardly from the surface of the elongated catheter member, whereby the extended annular ring can trap and hold a blood clot. The annular ring is currently preferably attached to the elongated, tubular catheter member such as by an adhesive, such as cyanoacrylate adhesive, for example, and is advantageously formed from a shape memory material. The annular ring is initially compressed axially and radially to be substantially flattened, for insertion through a guiding catheter to the treatment site in the vasculature, and the shape memory material of the annular ring has a desired compressed configuration at a temperature appropriate for introduction into the body via a catheter, and takes on an expanded configuration upon heat activation, for trapping and holding clots.

Figure 11:
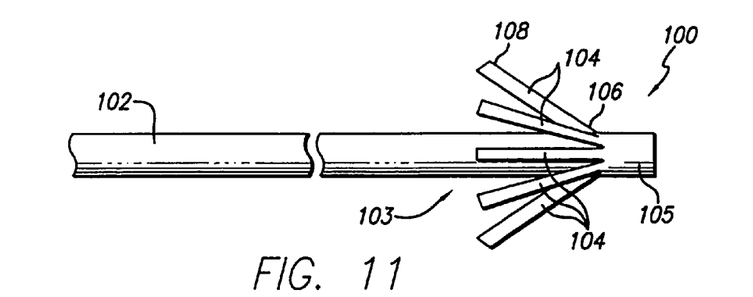
FIG. 11 is a side elevational view of a fifth preferred embodiment of a clot retrieval device according to the present invention, showing the clot retrieval members in an expanded state.
Figure 12:
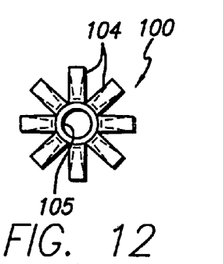
FIG. 12 is an end view of the clot retrieval device of FIG. 11, showing the clot retrieval members in an expanded state.
Figure 13:
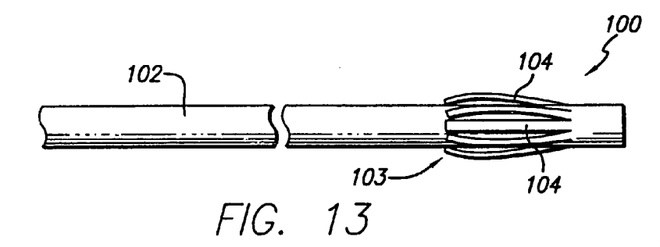
FIG. 13 is a side elevational view of the clot retrieval device of FIG. 11, showing the clot retrieval members in a compressed state.

A further presently preferred alternate embodiment is illustrated in FIGS. 11, 12 and 13 showing a clot retrieval apparatus 100 for removing clots from the vasculature of a patient. The clot retrieval apparatus includes an elongated, tubular catheter member 102, and a clot retrieval portion 103 having a plurality of tab members or fingers 104 projecting from the tubular wall 105 of the elongated catheter member, and having a first end 106 connected to the elongated catheter member, and a free end 108. In this embodiment, the tab members 104 are currently preferably attached to the elongated, tubular catheter member in an umbrella configuration such as by an adhesive, such as cyanoacrylate adhesive, for example, and are movable between an initial compressed configuration shown in FIGS. 12 and 13 in which the free ends of the tab members are substantially flattened radially against the exterior surface of the elongated catheter member, to an expanded configuration illustrated in FIG. 11, in which the tab members project outward radially from the surface of the elongated catheter member, whereby the extended tab members can trap and hold a blood clot. The elongated catheter member is adapted to be delivered through a guiding catheter as described above, for placement within a vessel of the patient when the tab members are in the compressed configuration, and the tab members and elongated catheter member are dimensioned to be removable from the vessel when the tab members are in the expanded configuration, so that clots trapped by the tab members can be withdrawn from the vessel. The tubular wall of the elongated tubular catheter member and the tab members are preferably formed from a shape memory material, and the tab members are initially compressed axially, radially, or both to be substantially flattened to extend substantially contiguously with the exterior surface of the tubular wall of the tubular catheter member.

Figure 14:
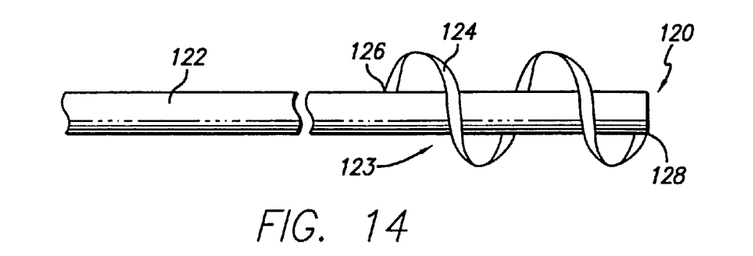
FIG. 14 is a side elevational view of a fifth preferred embodiment of a clot retrieval device according to the present invention, showing the clot retrieval member in an expanded state.
Figure 15:
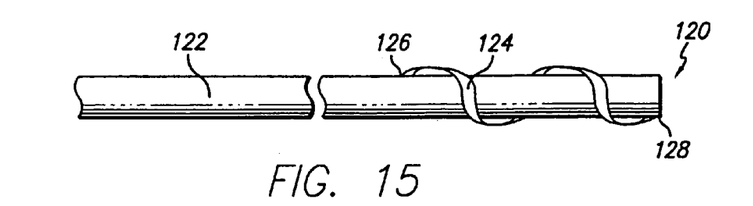
FIG. 15 is a side elevational view of the clot retrieval device of FIG. 14, showing the clot retrieval member in a compressed state.

A further presently preferred alternate embodiment is illustrated in FIGS. 14 and 15, illustrating a clot retrieval apparatus 120 for removing clots from the vasculature of a patient. In this embodiment, the clot retrieval apparatus includes an elongated, tubular catheter member 122, and a clot retrieval portion 123 formed from an elongated sheet or ribbon 124 of shape memory material having first and second ends 126 and 128 connected to the elongated catheter member such as by an adhesive, such as cyanoacrylate adhesive, for example. The elongated sheet of shape memory material is preferably wound in a helical configuration about the elongated catheter member, and has an initial compressed configuration illustrated in FIG. 15, in which the elongated sheet of shape memory material is compressed radially against the surface of the elongated catheter member, and an expanded configuration shown in FIG. 14, in which the elongated sheet of shape memory material projects outward radially from the surface of the elongated catheter member, whereby the extended elongated sheet of shape memory material can trap and hold a blood clot.

As is illustrated representatively in FIG. 3, in each of the foregoing embodiments, the shape memory clot retrieval members can advantageously be activated to move radially outwardly from a compressed configuration to an expanded configuration by a heat activation member 110 connected to a remote energy source (not shown) for heating the shape memory material clot retrieval members. The heat activation member is currently preferably an optical fiber, although other heat transmission members such as a heat pipe, or a device generating heat by RF energy, for example, may also be suitable. The heat activation member can be advanced axially through the middle of the tubular elongated catheter member to have a heat delivery portion 112 in close proximity adjacent to the clot retrieval members so that they can be activated at the desired treatment site.

In each of the foregoing embodiments, shape memory material preferably has a glass transition temperature ($T_g$) above body temperature, with a desired compressed configuration at a temperature appropriate for introduction into the body via a catheter, and an expanded configuration extending the one or more clot retrieval members outwardly upon heat activation. The shape memory material is currently preferably a shape memory polymer, such as polyurethane, heat shrink tubing such as polyethylene, polyethylene terephthalate (PET), or high density polyethylene (HDPE), although the shape memory material may alternatively be a shape memory metal such as nickel titanium alloy, such as that available under the trade name NITINOL, for example, that can be heat treated to have shape memory behavior. In one presently preferred embodiment, the shape memory material is a shape memory polymer distributed by Mitsubishi Heavy Industries, Ltd., that is a polyurethane-based material that undergoes a phase transformation at a manufactured temperature, Tg. After the shape memory polymer is cross-linked, the material is molded into its memory shape. The material becomes soft and formable at a temperature above Tg, and can be reshaped into another configuration by application of pressure to the material and cooling as the pressure is applied, to a temperature below Tg, fixing the new shape in the material as long as the temperature of the material remains below the Tg. When the temperature of the material again rises above the Tg, the material will return to its original memory shape.

It will be apparent from the foregoing that while particular forms of the invention have been illustrated and described, various modifications can be made without deparing from the spirit and scope of the invention. Accordingly, it is not intended that the invention be limited, except as by the appended claims.

What is claimed is:

1. An apparatus for removing clots from the vasculature of a patient, comprising:

an elongated catheter member with a tubular wall having an exterior surface; and a plurality of clot retrieval members defined on said exterior surface of said tubular wall of said elongated catheter member, said plurality of clot retrieval members being formed from a shape memory material having a glass transition temperature (Tg) above body temperature, the plurality of clot retrieval members being connected to said elongated catheter member, said clot retrieval members being movable from an initial compressed configuration to an expanded configuration extending outwardly from the elongated catheter member to trap and hold clots within the vessel, wherein said clot retrieval members are initially compressed axially to extend substantially contiguously with the surface of the tubular wall, the elongated catheter member being adapted to be placed within a vessel of the patient when the clot retrieval members are in the compressed configuration and removed from the vessel when the clot retrieval members are in the expanded configuration, whereby clots trapped by the clot retrieval members can be withdrawn from the vessel.

2. An apparatus for removing clots from the vasculature of a patient, comprising an elongated catheter member; and at least one clot retrieval member connected to said elongated catheter member, said at least one clot retrieval member being movable from an initial compressed configuration to an expanded configuration extending outwardly from the elongated catheter member to trap and hold clots within the vessel, the elongated catheter member being adapted to be placed within a vessel of the patient when the at least one clot retrieval member is in the compressed configuration and removed from the vessel when the clot retrieval member is in the expanded configuration, whereby clots trapped by the at least one clot retrieval member can be withdrawn from the vessel, said at least one clot retrieval member being formed from a shape memory material and having a glass transition temperature (Tg) above body temperature, said at least one clot retrieval member being connected to the elongated catheter member, with said at least one clot retrieval member having an initial compressed configuration in which said at least one clot retrieval member is compressed radially against the surface of the elongated catheter member and an expanded configuration in which said at least one clot retrieval member projects outwardly from the surface of the elongated catheter member, whereby said at least one clot retrieval member can trap and hold a blood clot.

3. The apparatus of claim 2, wherein said shape memory material has a desired compressed configuration at a temperature appropriate for introduction into the body via a catheter, and upon heat activation, will take on an expanded configuration for trapping and holding clots.

4. The apparatus of claim 2, wherein said shape memory material is selected from the group consisting of polyurethane, polyethylene, polyethylene terephthalate, and high density polyethylene.

5. The apparatus of claim 2, wherein said shape memory material comprises a nickel titanium alloy that can be heat treated to have shape memory behavior.

* * * * *